United States Patent [19]

Tang

[11] Patent Number: 4,968,830

[45] Date of Patent: Nov. 6, 1990

[54] AROMATIZATION PROCESS

[75] Inventor: David Y. Tang, East Amherst, N.Y.

[73] Assignee: Occidental Chemical Corporation, Niagara Falls, N.Y.

[21] Appl. No.: 405,607

[22] Filed: Sep. 11, 1989

[51] Int. Cl.$^5$ .............................................. C07B 35/04
[52] U.S. Cl. .................................... 558/425; 560/336; 562/493; 562/849; 562/865; 570/144; 570/146; 204/157.97
[58] Field of Search ....................... 558/425; 560/336; 562/493, 849, 865; 570/144, 146; 204/157.97

[56] References Cited

PUBLICATIONS

*Chemical Abstracts*, vol. 66 (1967); Abst. No. 115420s.
Mursakulov et al., *Zhurnal Org. Khimii*, vol. 22, No. 2, pp. 448–449, Feb. 1986.

*Primary Examiner*—Joseph Paul Brust
*Assistant Examiner*—M. S. Howard

*Attorney, Agent, or Firm*—James F. Tao; Arthur S. Cookfair

[57] ABSTRACT

Halogen substituted aromatic compounds of the formula

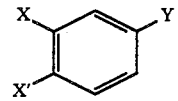

wherein Y is selected from the group $CO_2H$, COF, COCl, COBr, $CF_3$, CN, NCO, or F, and X and X' are independently hydrogen or a halogen selected from the group F-, Cl- and Br-, at least one of X and X' being halogen; may be prepared by the liquid phase reaction of a brominating agent, at temperatures below about 190° Celsius, with a correspondingly substituted cyclohexene or cyclohexadiene.

27 Claims, No Drawings

AROMATIZATION PROCESS

BACKGROUND OF THE INVENTION

This invention relates to a process for the preparation of substituted haloaromatic compounds by dehydrogenation of a corresponding halogen substituted saturated or partially saturated cyclic compound. The substituted halobenzene compounds are useful chemical intermediates for the synthesis of various commercial products, including polymers, dyes, pharmaceuticals, and agricultural chemical products.

Processes for the preparation of aromatic compounds by dehydrogenation of hydroaromatic compounds are known in the literature. Thus, for example, U.S. Pat. No. 3,883,599 discloses the preparation of thiophenols by dehydrogenating the corresponding cyclohexyl mercaptan by heating in the vapor state with sulfur dioxide, in the presence of a catalyst such as activated carbon, alumina, or chromium oxide on alumina.

The use of various dehydrogenation catalysts, including selenium, sulfur, and palladium on charcoal, in the dehydrogenation of hydroaromatic compounds is described by Fieser and Fieser, *Organic Chemistry*. third ed., Heath, Boston, 1956, at page 545.

U.S. Pat. No. 4,560,772 discloses the reaction of 4-methyltetrahydrophthalic anhydride with excess sulfur and a catalytic amount of zinc oxide and 2-mercaptobenzothiazole to produce 4-methylphthalic anhydride and hydrogen sulfide.

U.S. Pat. No. 4,560,773 discloses a similar reaction between the electron rich 4-methyl-tetrahydrophthalic anhydride and bromine in the presence of an acid acceptor such as dimethylformamide or pyridine in the liquid phase.

U.S. Pat. No. 4,709,056 discloses the dehydrohalogenation of dihalohexahydrophthalic anhydrides through the use of a basic alumina catalyst in a liquid phase to produce 4-fluoro-1,2,3,6-tetrahydrophthalic anhydride.

Ohkatou et al., *J. Jaoan Petrol. Inst.*, 22, 164–9 (1979) discloses the preparation of benzene by dehydrogenation of cyclohexane in the presence of activated carbon.

Bergmann *J. Amer. Chem. Soc.* 64, 176 (1942) discloses the aromatization of tetrahydrophthalic anhydride products of Diels-Alder reactions. The author discloses that dehydrogenation occurs when the tetrahydrophthalic anhydride product is boiled in nitrobenzene. However, it is further disclosed that dehydrogenation does not occur when p-bromonitrobenzene, p-chloronitrobenzene, or m-dinitrobenzene in xylene is employed.

U.S. Pat. No. 4,517,372 to Tang, disclose a process for the preparation of 4-fluorophthalic anhydride by dehydrogenation of gem-, difluoro- or gem-chlorofluoro- hexahydrophthalic anhydrides in the presence of a dehydrogenation catalyst, such as palladium.

U.S. Pat. No. 4,709,056 to Cotter, Lin, and Pawlak discloses the preparation of 4,4-difluorohexahydrophthalic anhydride and 4-chloro-4-fluorohexahydrophthalic anhydrides by reaction of hydrogen fluorides with 4-chlorotetrahydrophthalic anhydride.

Skvarchenko et al., *Obshchei Khimii*, Vol. 30, No. 11. pp. 3535–3541 disclose the aromatization of chloro-substituted tetrahydrophthalic anhydride by heating with phosphorus pentoxide. In the aromatization process described, however, decarboxylation also occurs with the formation of the corresponding chloro-substituted benzene compound. The preparation of various other tetrahydrophthali acids and anhydrides and various methods for dehydrogenation and aromatization thereof are reviewed by Skvarchenko in Russian Chemical Review. Vol 32, Nov. 1963, pp. 571–589.

Co-pending application Ser. No. 405,606, is directed to the preparation of halophthalic anhydrides by the liquid phase reaction of bromine with halotetrahydrophthalic anhydride or gem-dihalohexahydrophthalic anhydride.

The aromatization of organic compounds has been shown in the literature using various techniques and special catalysts. However, it will be apparent to those skilled in the art that a more efficient process for aromatization is desirable.

SUMMARY OF THE INVENTION

It has now been found that halogen substituted aromatic compounds the formula

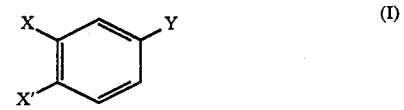

wherein Y is selected from the group $CO_2H$, COF, COCl, COBr, $CF_3$, CN, NCO, or F, and X and X' are independently hydrogen or a halogen selected from the group F-, Cl- and Br-, with the proviso that at least one of X and X' is halogen; may be prepared by the liquid phase reaction of a brominating agent, at temperatures below about 190° Celsius, with a halogen substituted cyclohexene or cyclohexadiene of the formula

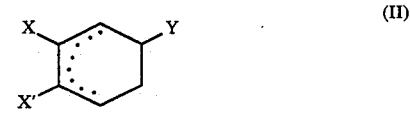

wherein X, X' and Y are as defined with the proviso that when X or X' are halogen, said halogen is directly attached to a double bond carbon.

DETAILED DESCRIPTION OF THE INVENTION

The starting reactants for the process of this invention, as represented by structural formula (11) above are halogen substituted cyclohexene or cyclohexadiene compounds such as those of the formulae

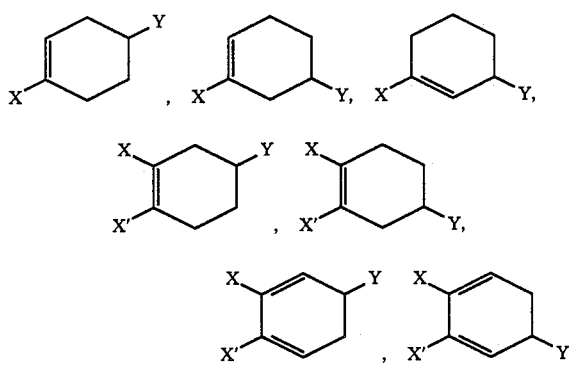

where X and X' independently represent H, F, Cl or Br; provided that at least one of X and X' is F, Cl or Br; and Y is $CO_2H$, COF, COCl, COBr, $CF_3$, CN, NCO, or F. The preferred brominating agent, based on process efficiency and economic considerations, is elemental bromine. Other brominating agents which may be employed include, for example, N-bromosuccinimide and bromine chloride. The brominating agent is preferably employed in at least stoichiometric amounts, that is two moles of brominating agent per mole of cyclohexene reactant, or four moles of bromine per mole of cyclohexadiene reactant, and most preferably in an amount of up to about 10 percent excess of that stoichiometric amount.

The cyclohexene or cyclohexadiene reactants (formula II) that may be employed in the process of the invention include, for example, 1-chloro-4-carboxyl-cyclohex-1-ene
1-chloro-3-carboxyl-cyclohex-1-ene
1-bromo-3-isocyanato-cyclohex-1-ene
1-bromo-5.isocyanato-cyclohex-1-ene
1-fluoro-4-cyano-cyclohex-1-ene
1-fluoro-4-chloroformyl-cyclohex-1-ene
1,4-difluoro-cyclohex-1-ene
1-chloro-4-trifluoromethyl-cyclohex-1-ene
1-fluoro-5-trifluoromethyl-cyclohex-1-ene
1,2-dichloro-4-cyano-cyclohex-1-ene
1,2-difluoro-4-cyano-cyclohex-1-ene
1-chloro-2-fluoro-4-cyano-cyclohex-1-ene
3-chloro-2-fluoro--5-cyano-cyclohex-1,3-diene
2,3-dichloro-5-carboxyl-cyclohex-1,3-diene The process is carried out in the liquid phase, either neat or in the presence of a solvent, at atmospheric pressure or under applied or autogenous pressure at temperatures ranging from about 0° to about 190° Celsius and preferably about 70° to about 170° Celsius. Solvents that may be employed are preferably substantially non-reactive to bromine as well as to the organic reactant and preferably are characterized by a boiling point greater than about 100° Celsius. Typical of the solvents that may be employed are bromobenzenes and chlorobenzenes. The most preferred solvent is monochlorobenzene. Lower boiling solvents, such as chloroform, carbon tetrachloride, or chlorinated ethanes may be advantageously employed when the process is carried out at lower temperatures, in the presence of a free radical initiator.

The process of the invention involves a free radical reaction which may be enhanced by the use of a free radical initiator such as visible or ultra-violet irradiation, or addition of catalytic amounts, typically less than about 5 percent by weight, based on weight of reactants, of initiators such as azo compounds, peroxides and the like. Typical azo compounds useful as free-radical initiators are azobis (alpha, gamma-dimethyl valeronitrile), 2,2'-azobis (2,4-dimethyl valeronitrile); and typical peroxides are benzoyl peroxide, diacetyl peroxide, diisopropyl peroxydicarbonate, lauroyl peroxide and the like. Azobisisobutyronitrile is particularly useful in the process of this invention. When the process is carried out in the presence of a free radical initiator, lower temperatures, typically in the range of about 0° to about 100° Celsius, may be employed.

During the reaction it is preferred to condense the exiting vapors at a temperature sufficient to condense bromine, but allow HBr to escape (to be recovered by scrubbers for subsequent re-use).

The following specific examples are provided to further illustrate this invention and the manner in which is may be carried out. It will be understood, however, that the specific details given in the examples have been chosen for purposes of illustration and are not to be construed as a limitation on the invention. In the examples, unless otherwise indicated, all parts and percentages are by weight and all temperature are in degrees Celsius.

EXAMPLE 1

To a 25 ml three-necked flask equipped with an equal pressure additional funnel, a dry-ice condenser with a gas outlet and a stopper, is charged 14.2 g (0.1 mole) of 1-chloro-4-cyanocyclo-hex-1-ene (I) and 3 g of chlorobenzene The mixture is heated to 90°-100° C. with stirring. Bromine, 32 g (0.2 mole), is added dropwise, sub-surface. The reddish-brown color dissipates quickly and a gas evolution occurs. When approximately 24 g of bromine has been added, the pot temperature is raised to 120°-130° C. The remaining bromine is added in the same fashion. The pot temperature may then be raised to 150°-160° C. for 2-4 hours. During this period, an additional amount of bromine, such as about 1-2 g, may be added to complete the conversion of (I). A good yield of 4-chlorobenzonitrile will be obtained by the fractional distillation of the mixture.

EXAMPLE 2

To a 25 ml three-necked flask equipped with an equal pressure additional funnel, a dry-ice condenser with a gas outlet and a stopper, is charged 17.9 g (0.1 mole) of 1-chloro-4-chloroformyl cyclohex-1-ene (I). The solution is heated to 90°-100° C. with stirring, using a magnetic stirring bar. Bromine, 32 g (0.2 mole), is added dropwise, sub-surface. The color dissipates quickly and a gas evolution occurs. When about 24 g of bromine has been added, the pot temperature is raised to 120°-130° C. The remaining bromine is added in the same fashion. The pot temperature may then be raised to 150°-160° C. fro 2-4 hours. During this period, an additional amount of bromine, such as about 1-2 g, may be added to complete the conversion of (I). A good yield of 4-chlorobenzoyl chloride will be obtained by the fractional distillation of the mixture.

EXAMPLE 3

To a 25 ml three-necked flask equipped with an equal pressure additional funnel, a dry-ice condenser with a gas outlet and a stopper, is charged 18.5 g (0.1 mole) 1-chloro-4-trifluoromethylcyclohex-1-ene (I).

The solution is heated to 60°-70° C. with stirring, using a magnetic stirring bar. Bromine, 32 g (0.2 mole), is added dropwise sub-surface. The reddish color dissipates quickly and a gas evolution occurs. A catalytic amount of radical initiator such as azodiisobutyronitrile may be added intermittently to promote the reaction. When the color begins to sustain, the pot temperature is raised to 90°-100° C. The remaining bromine is added in the same fashion. The pot temperature can be raised to 110°-120° C. for 2-4 hours. During this period, an additional amount of bromine such as 1-2 g may be added to complete the conversion of (I). 4-chlorobenzotrifluoride can be obtained in a good yield by fractional distillation of the mixture.

What is claimed is:

1. A process for the preparation of halogen substituted aromatic compounds of the formula

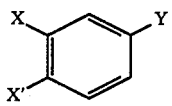

(I)

wherein Y is selected from the group $CO_2H$, COF, COCl, COBr, $CF_3$, CN, NCO, or F, and X and X, are independently hydrogen or a halogen selected from the group F-, Cl- and Br-, with the proviso that at least one of X and X' is halogen; which comprises reacting in the liquid phase, at temperatures below about 190 Celsius, a brominating agent with a halogen substituted cyclohexene or cyclohexadiene of the formula

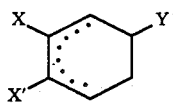

(II)

wherein X, X' and Y are as defined with the proviso that when X or X' are halogen, said halogen is directly attached to a double bond carbon.

2. A process accoding to claim 1 wherein at least one of X or X' is hydrogen.

3. A process according to claim 2 wherein Y is $CO_2H$.

4. A process according to claim 2 wherein Y is COF.
5. A process according to claim 2 wherein Y is COCl.
6. A process according to claim 2 wherein Y is COBr.
7. A process according to claim 2 wherein Y is $CF_3$.
8. A process according to claim 2 wherein Y is CN.
9. A process according to claim 2 wherein Y is NCO.
10. A process according to claim 2 wherein Y is F.

11. A process according to claim 1 wherein both X and X' are halogen.

12. A process according to claim 11 wherein Y is $CO_2H$.

13. A process according to claim 11 wherein Y is COF.

14. A process according to claim 11 wherein Y is COCl.

15. A process according to claim 11 wherein Y is COBr.

16. A process according to claim 11 wherein Y is $CF_3$.

17. A process according to claim 11 wherein Y is CN.

18. A process according to claim 11 wherein Y is NCO.

19. A process according to claim 11 wherein Y is F.

20. A process according to claim 1 wherein the brominating agent is elemental bromine.

21. A process according to claim 1 wherein the brominating agent is N-bromosuccinimide.

22. A process according to claim 1 carried out neat.

23. A process according to claim 1 carried out in the presence of a solvent.

24. A process according to claim 1 carried out in the presence of a free radical initiator.

25. A process for the preparation of 4-chlorobenzonitrile which comprises reacting bromine with 1-chloro-4-cyano-cyclohex-1-ene in the liquid phase at a temperature below about 190° Celsius.

26. A process for the preparation of 4-chlorobenzoyl chloride which comprises reacting bromine with 1-chloro-4-chloroformy cyclohex-1-ene, in the liquid phase at a temperature of below about 190° Celsius.

27. A process for the preparation of 4-chlorobenzotrifluoride which comprises reacting bromine with 1-chloro-4-trifluoromethylcyclohex-1-ene, in the liquid phase at a temperature of below about 190° Celsius.

* * * * *